(12) United States Patent
Brown (10) Patent No.: US 7,169,610 B2
(45) Date of Patent: Jan. 30, 2007

(54) SERUM-FREE MEDIA FOR CHONDROCYTES AND METHODS OF USE THEREOF

(75) Inventor: Liesbeth Maria E. Brown, West Newton, MA (US)

(73) Assignee: Genzyme Corporation, Cambridge, MA (US)

( * ) Notice: Subject to any disclaimer, the term of this patent is extended or adjusted under 35 U.S.C. 154(b) by 302 days.

(21) Appl. No.: 10/350,816

(22) Filed: Jan. 24, 2003

(65) Prior Publication Data

US 2003/0211604 A1 Nov. 13, 2003

Related U.S. Application Data

(60) Provisional application No. 60/389,078, filed on Jun. 14, 2002, provisional application No. 60/351,949, filed on Jan. 25, 2002.

(51) Int. Cl.
*C12N 5/00* (2006.01)

(52) U.S. Cl. .................. 435/404; 435/325; 435/366; 435/405; 435/406

(58) Field of Classification Search ............ 435/404, 435/405, 406, 325, 366
See application file for complete search history.

(56) References Cited

U.S. PATENT DOCUMENTS

| | | | | |
|---|---|---|---|---|
| 5,723,331 | A | * | 3/1998 | Tubo et al. .................. 435/366 |
| 5,871,779 | A | * | 2/1999 | Cruz .......................... 424/646 |
| 5,904,717 | A | * | 5/1999 | Brekke et al. .............. 424/423 |
| 6,001,352 | A | * | 12/1999 | Boyan et al. ............... 424/93.7 |
| 6,150,163 | A | | 11/2000 | McPherson et al. |
| 6,153,582 | A | * | 11/2000 | Skelnik ....................... 514/12 |
| 6,365,405 | B1 | | 4/2002 | Salzmann et al. |
| 2002/0041900 | A1 | | 4/2002 | Olsen et al. |

FOREIGN PATENT DOCUMENTS

| | | | |
|---|---|---|---|
| WO | WO 98/59035 | * | 12/1998 |
| WO | WO00/27996 | | 5/2000 |
| WO | WO01/57083 | | 8/2001 |

OTHER PUBLICATIONS

Freshney, R. Ian, "Culture of Animal Cells: A Manual of Basic Techniques", 2nd ed. A. R. Liss, Inc. New York (1987), pp. 137-168.
Freshney, R. Ian, "Culture of Animal Cells: A Manual of Basic Techniques", 3rd ed. John Wiley & Sons, Inc. New York (1994) pp. 91-99.
Eagle, "Nutrition Needs of Mammalian Cells in Tissue Culture", *Science*, (1955), vol. 122, No. 3168, pp. 501-504.
McCoy et al., "Amino Acid Requirements of the Novikoff Hepatoma *in vitro*", *Proceedings of the Society for Experimental Biology and Medicine*, (1959), vol. 100, pp. 115-118.
Dulbecco et al., "Plaque Production by the Polyoma Virus", *Virology*, (1959) No. 8, pp. 396-397.
Waymouth, "Rapid Proliferation of Sublines of NNCTC Clone 929 (Strain L) Mouse Cells in a Simple Chemically Defined Medium (MB 752/1)", *National Cancer Institute*, (1959) vol. 22, pp. 1003-1017.
Ham, "An Improved Nutrient Solution For Diploid Chinese Hamster and Human Cell Lines", *Experimental Cell Research* (1963), vol. 29, pp. 515-526.
Leibovitz, "The Growth and Maintenance of Tissue-Cell Cultures in Free Gas Exchange with the Atmosphere", *American Journal of Hygiene* (1963) vol. 78, pp. 173-180.
Evans et al., "Chemically Defined Media For Cultivation of Long-Term Cell Strains From Four Mammalian Species", *Experimental Cell Research* (1964) vol. 36, pp. 439-474.
Moore et al., "Culture of Normal Human Leukocytes", Journal of the American Medical Association, (1967) vol. 199, No. 8, pp. 519-524.
Williams et al., "Isolation and Long-Term Cell Culture of Epithelial-like Cells from Rat Liver", *Experimental Cell Research* (1971), vol. 69 pp. 106-112.
Klagsburn, "Large-Scale Preparation of Chondrocytes", Methods in Enzymology (1979) vol. 58, pp. 560-564.
Jennings et al., "Clonal growth of primary cultures of rabbit ear chondrocytes in a lipid-supplemental defined medium"., *Experimental Cell Research*, (1983), vol. 145, pp. 415-423.
Johnsson et al., "The c-*sis* gene encodes a precursor of the b chain of platelet-derived growth factor" *The EMBO Journal* (1984), vol. 3, No. 5 pp. 921-927.
Adolphe et al., "Cell Multiplication and Type II Collagen Production by Rabbit Articular Chondrocytes Cultivated in a Defined Medium", *Exp. Cell Research*, (1984), vol. 155, pp. 527-536.
Raines et al., "Purification of Human Platelet-Derived Growth Factor", Methods in Enzymology (1985) vol. 109, pp. 749-773.
Farndale et al., "Improved quantitation and discrimination of sulphated glycosaminoglycans by use of dimethylmethylene blue", *Biochimica et Biophysica Acta*, (1986), vol. 883, pp. 173-177.
Freshney "Culture of Animal Cells: A Manual of Basic Techniques", 2nd ed. A. R. Liss, Inc. New York (1987), pp. 91-99 and 137-168.
Aulthouse et al., "Expression of the human chondrocyte phenotype in vitro". *In Vitro Cellular and Development Biology*, Jul. 1989, vol. 25, No. 7, pp. 659-668.
Weiss et al., "Growth of Insect Cells in a Serum-Free Medium and Production of Recombinant Proteins Using Various Bioreactors", *In Vitro* (1990) vol. 26, p. 30A (Abstract).
Gorfien et al., "A New Serum-free Medium for Growth of Chinese Hamster Ovary (CHO) Cells and Production of rDNA Proteins", *In Vitro* (1990) vol. 26, p. 37A (Abstract).

(Continued)

*Primary Examiner*—Leon B. Lankford, Jr.
(74) *Attorney, Agent, or Firm*—Robert J. Cobert (57) ABSTRACT

The present invention provides defined serum-free cell culture media useful in culturing fibroblasts, especially articular chondrocytes, that avoids problems inherent in the use of serum-containing media. The defined media comprise platelet-derived growth factor (PDGF), and chemically defined lipids, or combinations of these compounds. In another aspect, the present invention also provides tissue culture methods that comprise incubating chondrocytes in the defined serum free media. The methods enhance attachment and proliferative expansion of chondrocytes seeded at low density while maintaining their redifferentiation potential.

17 Claims, 4 Drawing Sheets

OTHER PUBLICATIONS

Fike et al., "Enhancement of Monoclonal Antibody Production In Vitro" *In Vitro* (1990), vol. 26, p. 54A (Abstract).

Bonaventure et al., "Reexpression of cartilage specific genes by dedifferentiated human articular chondrocytes cultured in alginate beads", *Experimental Cell Research*, (1994), vol. 212, pp. 97-104.

Brittberg et al., "Treatment of deep cartilage defects in the knee with autologous chondrocyte transplantation"., *The New England Journal of Medicine*, Oct. 6, 1994, vol. 331, No. 14, pp. 889-895.

Shortkroff, et al., "Healing of chondral and osteochondral defects in a canine model: the role of cultured chondrocytes in regeneration of articular cartilage", Biomaterials (1996) vol. 17, pp. 147-154.

Reno et al. "Rapid Isolation of Total RNA from Small Samples of Hypocellular, Dense Connective Tissues", Biotechniques (1997) vol. 22, pp. 1082-1086.

\* cited by examiner

SERUM-FREE MEDIA FOR CHONDROCYTES AND METHODS OF USE THEREOF

This application claims the right to priority based on U.S. provisional applications Nos. 60/389,078, filed on Jun. 14, 2002, and 60/351,949, filed Jan. 25, 2002.

FIELD OF THE INVENTION

The present invention relates to the field of cell and tissue culture. More specifically, the invention relates to methods and compositions for ex vivo propagation of cells capable of forming cartilaginous tissue intended for treatment or repair of cartilage defects.

BACKGROUND OF THE INVENTION

Articular cartilage is composed of chondrocytes encased within the complex extracellular matrix produced by these cells. The unique biochemical composition of this matrix provides for the smooth, nearly frictionless motion of articulating surfaces of the knee joint. With age, tensile properties of human articular cartilage change as a result of biochemical changes. After the third decade of life, the tensile strength of articular cartilage decreases markedly. Damage of cartilage produced by trauma or disease, e.g., rheumatoid and osteoarthritis, can lead to serious physical debilitation.

The inability of cartilage to repair itself has led to the development of several surgical strategies to alleviate clinical symptoms associated with cartilage damage. More than 500,000 arthroplastic procedures and joint replacements are performed annually in the United States alone. Autologous chondrocyte implantation is a procedure that has been approved for treatment of articular cartilage defects. The procedure involves harvesting a piece of cartilage from a non-weight bearing part of the femoral condyle and propagating the isolated chondrocytes ex vivo for subsequent implantation back into the same patient (Brittberg et al. (1994) *New England J. of Medicine*, 331: 889–895).

Articular chondrocytes express articular cartilage-specific extracellular matrix components. Once articular chondrocytes are harvested and separated from the tissue by enzymatic digestion, they can be cultured in monolayers for proliferative expansion. However, during tissue culture, these cells become phenotypically unstable, adopt a fibroblastic morphology, and then cease to produce type II collagen and proteoglycans characteristic of hyaline-like articular cartilage. Such "dedifferentiated" cells proliferate rapidly and produce type I collagen, which is characteristic of fibrous tissue. Nevertheless, when placed in an appropriate environment such as suspension culture medium in vitro (Aulthouse et al. (1989) *In Vitro Cell. & Devel. Biology*, 25: 659–668) or in the environment of a cartilage defect in vivo (Shortkroff et al. (1996) *Biomaterials*, 17: 147–154), the cells redifferentiate, i.e., express articular cartilage-specific matrix molecules again. The reversibility of dedifferentiation is key to the successful repair of articular cartilage using cultured autologous chondrocytes.

Human chondrocytes are typically cultured in Dulbecco's Modified Eagle's Medium (DMEM) supplemented with 10% (v/v) fetal bovine serum (FBS) (Aulthouse et al. (1989) *In Vitro Cell. & Devel. Biology*, 25: 659–668; Bonaventure et al. (1994) *Exp. Cell Res.*, 212: 97–104). However, even though serum is widely used for mammalian cell culture, there are several problems associated with its use (Freshney (1994) Serum-free media. *In Culture of Animal Cells*, John Wiley & Sons, New York, 91–99): 1) serum contains many unidentified or non-quantified components and therefore is not "defined;" 2) the composition of serum varies from lot to lot, making standardization difficult for experimentation or other uses of cell culture; 3) many of the serum components affect cell attachment, proliferation, and differentiation making it difficult to control these parameters; 4) some components of serum are inhibitory to the proliferation of specific cell types and to some degree may counteract its proliferative effect, resulting in sub-optimal growth; and 5) serum may contain viruses and other pathogens which may affect the outcome of experiments or provide a potential health hazard if the cultured cells are intended for implantation in humans.

Thus, the use of defined serum-free media is particularly advantageous in the ex vivo expansion of chondrocytes for treatment of cartilage defects. However, such defined serum-free media must be sufficient for attachment of adult human articular chondrocytes seeded at low density, sustain proliferation until confluent cultures are attained, and maintain the capacity of chondrocytes to re-express the articular cartilage phenotype.

There has been some effort to develop biochemically defined media (DM) for cell culture. DM generally includes nutrients, growth factors, hormones, attachment factors, and lipids. The precise composition must be tailored for the specific cell type for which the medium is designed. Successful growth of some cell types, including fibroblasts, keratinocytes, and epithelial cells has been achieved in various DM (reviewed by Freshney, 1994). However, attachment and proliferation of cells in the known media are often not optimal.

Additionally, the amounts of starting cell material available for autologous chondrocyte implantation are generally limited. Therefore, it is desirable to seed articular chondrocytes at a minimal subconfluent density. Attempts to culture articular chondrocytes at subconfluent densities in DM have been only partially successful. Although DM that can sustain the proliferative capacity of the chondrocytes seeded at low density have been developed, the use of these media still requires serum for the initial attachment of cells to the tissue culture vessel after seeding (Adolphe et al. (1984) *Exp. Cell Res.*, 155: 527–536, and U.S. Pat. No. 6,150,163).

A need exists to optimize, standardize, and control conditions for attachment, proliferation and maintenance of redifferentiation-capable chondrocytes for use in medical applications, especially, in humans.

SUMMARY OF THE INVENTION

It is an object of the invention to provide safe, effective, and inexpensive culture medium compositions and methods for culturing articular chondrocytes.

It is another object of the invention to provide a method for culturing articular chondrocytes which does not involve the use of serum.

It is yet another object of the invention to provide a simple method for culturing articular chondrocytes in a single defined cell culture medium.

It is yet another object of the invention to provide a method for culturing articular chondrocytes under serum-free conditions, wherein chondrocytes are seeded at low subconfluent densities.

Still another object of the invention is to provide a method for ex vivo expansion of articular chondrocytes, in which the cells retain their redifferentiation capacity.

The invention provides a method for culturing human articular chondrocytes and compositions of chemically defined culture media. The DM of the invention avoid the use of serum at any stage of chondrocyte culture and enhance cell attachment and proliferation under serum-free conditions while maintaining the capacity of chondrocytes to re-express cartilage-specific phenotype.

One aspect of the invention provides defined cell culture media that are sufficient for the initial attachment of cells to a culture substratum, thereby eliminating a need for a serum-containing medium in the initial stage of cell culture. Another aspect of the invention provides defined serum-free cell culture media that promote proliferation of chondrocytes without use of serum at any stage during cell culture. Yet another aspect of the invention provides cell culture media that may be used to prime chondrocytes prior to implantation into a subject or included as a redifferentiation-sustaining medium to chondrocytes embedded in a matrix intended for implantation into cartilage defects.

In certain embodiments, the DM of the invention comprises a basal medium. In one embodiment, the basal medium is prepared using commercially available culture media such as DMEM, RPMI-1640, and Ham's F-12. In one embodiment, DMEM, RPMI-1640, and Ham's F-12 are mixed at a 1:1:1 ratio and combined with growth supplements to produce the basal medium defined in Table 3 (referred to hereinafter as cDRF). In addition to a basal medium, the DM of the invention comprises at least two of the supplements selected from the group consisting of: platelet-derived growth factor (PDGF), and one or more lipid components selected from the group consisting of stearic acid, myristic acid, oleic acid, linoleic acid, palmitic acid, palmitoleic acid, arachidonic acid, linolenic acid, cholesterol, and alpha-tocopherol acetate. In a particular embodiment, DM comprises PDGF and at least one lipid component. In related embodiments, DM comprises PDGF and at least two, four, six, eight, or all of the lipid components set forth in Table 4. In a further embodiment, the PDGF is PDGF-BB. In certain embodiments, the concentration of PDGF is chosen from 0.1–1 ng/ml, 1–5 ng/ml, 5–10 ng/ml, 10 ng/ml, 10–15 ng/ml, 15–50 ng/ml, and 50–100 ng/ml. In certain other embodiments, the concentration (v/v) of lipid components is chosen from 0.05–0.1%, 0.1–0.5%, 0.5%, 0.5–1%, 1–2%, and 2–5%.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

DETAILED DESCRIPTION OF THE INVENTION

This invention provides a method for culturing chondrocytes in a defined serum-free media and is based, at least in part, on the discovery that the basal medium referred to as cDRF, as described below, when supplemented with PDGF and at least on of the lipids set forth in Table 4, is sufficient for attachment, proliferation and maintenance of redifferentiation-capable chondrocytes in culture and can substitute for a serum-containing medium in all stages of cell culture.

Preparation of Basal Medium (cDRF)

The first step in preparing defined, serum media (DM) of the invention is to prepare a basal medium. In a particular embodiment, the basal medium defined in Table 3 (cDRF), is prepared from commercially available starting components as described below. cDRF is a modification of the DM developed by Adolphe et al. (1994) and by McPherson et al. (U.S. Pat. No. 6,150,163).

The three starting components of cDRF are DMEM, RPMI-1640, and Ham's F12 (Gibco BRL, Grand Island, N.Y.). The precise composition of each of these starting components is set forth in Table 1. The starting components are combined at a 1:1:1 ratio. The resulting medium (defined in Table 2 and referred to as DRF) is then supplemented with ITS (10 µg/ml insulin, 5.5 µg/ml transferrin, 7 ng/ml selenium, and, optionally, 2.0 µg/ml ethanolamine), human fibronectin (Collaborative Biomedical Products, Bedford, Mass.), human serum albumin (HSA), linoleic acid, human basic fetal growth factor (bFGF) (R&D Systems, Minneapolis, Minn.), gentamycin (BioWhittaker, Walkersville, Md.), and hydrocortisone (Sigma, St. Louis, Mo.) to create cDRF. Freshly prepared incomplete cDRF (cDRF without bFGF, fibronectin, linoleic acid, and HSA) can be stored in the dark up to 2 weeks at 2–8° C. bFGF, fibronectin, and HSA supplemented with linoleic acid are diluted into the medium to create cDRF on the day of use for cell culture. HSA utilized in the media of the invention is either purified from human plasma (Grifols® HSA, SeraCare, Oceanside, Calif.) or recombinant (New Century Pharmaceuticals, Huntsville, Ala.). All materials are reconstituted, diluted, and stored as per suppliers' recommendations.

The term "basal medium" is used interchangeably with "defined basal medium" and refers to any medium that comprises all essential components of cDRF listed in Table 3. A component or a subset of components listed in Table 3 is non-essential if, when its concentration is reduced, or the component is eliminated, the properties of the medium related to chondrocyte attachment, proliferation, and redifferentiation, remain substantially the same. The stated concentrations of individual components may be adjusted for specific cell culture conditions. Such adjustments can easily be made by a person skilled in the art using routine techniques. It will also be understood that additional components may be added to the medium if such components are desirable and do not negatively impact on chondrocytes attachment, proliferation, and redifferentiation. Such components include growth factors, lipids, serum proteins, vitamins, minerals, carbohydrates. For example, it may be advantageous to supplement the medium with growth factors or hormones that promote chondrocyte redifferentiation such as TGF-β (TGF-β1, -β2, -β3), IGF, and insulin, as described in U.S. Pat. No. 6,150,163. Such growth factors and hormones are commercially available. Additional examples of supplements include, but are not limited to, bone morphogeneteic proteins (BMP), of which there are at least 15 structurally and functionally related proteins. BMP have been shown to be involved in the growth, differentiation, chemotaxis, and apoptosis of various cell types. Recombinant BMP-4 and BMP-6, for example, can be purchased from R&D Systems (Minneapolis, Minn.; catalog # 314-BP and 507-BP, respectively). The concentration of various supplements in DM of the invention can be determined without undue experimentation. The concentration of BMP in DM of the invention is chosen from 0.01–0.1 ng/ml, 0.1–1 ng/ml, 1–10 ng/ml, 100 ng/ml, 10–50 ng/ml, 50–100 ng/ml, and 0.1–1 µg/ml.

A skilled artisan will appreciate that DM of the invention have advantages in addition to avoiding the use of serum. Thus, it may be desirable to utilize DM of the invention in applications where the use of undefined components is acceptable. Consequently, DM of the invention may be supplemented with serum e.g., fetal calf serum, or other chemically undefined components such as, for example, animal or plant tissue extracts. In certain embodiments, the DM of the invention may be supplemented with 10% or less than 8%, 6%, 4%, 2%, or 1% of serum.

A skilled artisan will also appreciate that equivalents of cDRF may be prepared from a variety of known media, e.g., Basal Medium Eagle medium (Eagle, *Science,* 122: 501, 1955), Minimum Essential medium (Dulbecco et al., *Virology,* 8: 396,1959), Ham's medium (Ham, *Exp. Cell Res.,* 29: 515,1963), L-15 medium (Leibvitz, *Amer. J. Hyg.,* 78:173, 1963), McCoy 5A medium (McCoy et al., *Proc. Exp. Biol. Med.,* 100: 115,1959), RPMI medium (Moore et al., *J. A. M. A.,* 199: 519, 1967), Williams' medium (Williams, *Exp. Cell Res.,* 69:106–112,1971), NCTC 135 medium (Evans et al., *Exp. Cell Res.,* 36: 439,1968), Waymouth's medium MB752/1 (Waymouth, *Nat. Cancer Inst.,* 22: 1003, 1959), etc. These media may be used singularly or as mixtures in suitable proportions to prepare a basal medium equivalent to cDRF. Alternatively, cDRF or its equivalent can be prepared from individual chemicals or from other media and growth supplements. The invention is not limited to media of any particular consistency and encompasses the use of

TABLE 1

Compositions of Starting Media

| | DMEM 1× Liquid, mg/L | RPMI-1640 1× Liquid, mg/L | Ham's F-12 1× Liquid, mg/L |
|---|---|---|---|
| Inorganic Salts | | | |
| $CaCl_2$ (anhyd.) | 200.00 | | 33.22 |
| $Ca(NO_3)_2.4H_2O$ | | 100.00 | |
| $CuSO_4.5H_2O$ | | | 0.0024 |
| $Fe(NO_3)_2.9H_2O$ | 0.10 | | |
| $FeSO_4.7H_2O$ | | | 0.83 |
| KCl | 400.00 | 400.00 | 223.60 |
| $MgSO_4$ (anhyd.) | 97.67 | 48.84 | |
| $MgCl_2$ (anhyd.) | | | 57.22 |
| NaCl | 6400.00 | 6000.00 | 7599.00 |
| $NaHCO_3$ | 3700.00 | 2000.00 | 1176.00 |
| $NaH_2PO_4.H_2O$ | 125.00 | | |
| $Na_2HPO_4$ (anhyd.) | | 800.00 | 142.00 |
| $ZnSO_4.7H_2O$ | | | 0.86 |
| Other Components | | | |
| D-Glucose | 4500.00 | 2000.00 | 1802.00 |
| Glutathione (reduced) | | 1.00 | |
| Hypoxanthine Na | | | 4.77 |
| Linoleic Acid | | | 0.084 |
| Lipoic Acid | | | 0.21 |
| Phenol Red | 15.00 | 5.00 | 1.20 |
| Putrescine 2HCl | | | 0.161 |
| Sodium Pyruvate | | | 110.00 |
| Thymidine | | | 0.70 |
| Amino Acids | | | |
| L-Alanine | | | 8.90 |
| L-Arginine | | 200.00 | |
| L-Arginine.HCl | 84.00 | | 211.00 |
| $L-Asparagine.H_2O$ | | | 15.01 |
| L-Asparagine (free base) | | 50.00 | |
| L-Aspartic Acid | | 20.00 | 13.30 |
| L-Cystine.2HCl | 63.00 | 65.00 | |
| $L-Cysteine.HCl.H_2O$ | | | 35.12 |
| L-Glutamic Acid | | 20.00 | 14.70 |
| L-Glutamine | 584.00 | 300.00 | 146.00 |
| Glycine | 30.00 | 10.00 | 7.50 |
| $L-Histidine.HCl.H_2O$ | 42.00 | | 21.00 |

TABLE 1-continued

Compositions of Starting Media

| | DMEM 1× Liquid, mg/L | RPMI-1640 1× Liquid, mg/L | Ham's F-12 1× Liquid, mg/L |
|---|---|---|---|
| L-Histidine (free base) | 1.00 | 5.00 | |
| L-Hydroxyproline | | 20.00 | |
| L-Isoleucine | 105.00 | 50.00 | 4.00 |
| L-Leucine | 105.00 | 50.00 | 13.10 |
| L-Lysine.HCl | 146.00 | 40.00 | 36.50 |
| L-Methionine | 30.00 | 15.00 | 4.50 |
| L-Phenylalanine | 66.00 | 15.00 | 5.00 |
| L-Proline | | 20.00 | 34.50 |
| L-Serine | 42.00 | 30.00 | 10.50 |
| L-Threonine | 95.00 | 20.00 | 11.90 |
| L-Tryptophan | 16.00 | 5.00 | 2.00 |
| L-Tyrosine.2Na$_2$H$_2$O | 104.00 | 29.00 | 7.81 |
| L-Valine | 94.00 | 20.00 | 11.70 |
| Vitamins | | | |
| Biotin | | 0.20 | 0.0073 |
| D-Ca pantothenate | 4.00 | 0.25 | 0.50 |
| Choline Chloride | 4.00 | 3.00 | 14.00 |
| Folic Acid | 4.00 | 1.00 | 1.30 |
| I-Inositol | 7.20 | 35.00 | 18.00 |
| Niacinamide | 4.00 | 1.00 | 0.036 |
| Para-aminobenzoic Acid | | 1.00 | |
| Pyridoxine HCl | | 1.00 | 0.06 |
| Pyridoxal HCl | 4.00 | | |
| Riboflavin | 0.40 | 0.20 | 0.037 |
| Thiamine HCl | 4.00 | 1.00 | |
| Vitamin B$_{12}$ | | 0.005 | 1.40 |

TABLE 2

Composition of DRF

| Inorganic Salts | 3× Liquid, mg/L |
|---|---|
| CaCl$_2$ (anhyd.) | 233.22 |
| Ca(NO$_3$)$_2$.4H$_2$O | 100.00 |
| CuSO$_4$.5H$_2$O | 0.0024 |
| Fe(NO$_3$)$_2$.9H$_2$O | 0.10 |
| FeSO$_4$.7H$_2$O | 0.83 |
| KCl | 1023.60 |
| MgSO$_4$ (anhyd.) | 146.51 |
| MgCl$_2$ (anhyd.) | 57.22 |
| NaCl | 19999.00 |
| NaHCO$_3$ | 6876.00 |
| NaH$_2$PO$_4$.H$_2$O | 125.00 |
| Na$_2$HPO$_4$ (anhyd.) | 942.00 |
| ZnSO$_4$.H$_2$O | 0.86 |
| Other Components | |
| D-Glucose | 8302.00 |
| Glutathione (reduced) | 1.00 |
| Hypoxanthine.Na | 4.77 |
| Linoleic Acid | 0.084 |
| Lipoic Acid | 0.21 |
| PhenolRed | 21.20 |
| Putrescine 2HCl | 0.161 |
| Sodium Pyruvate | 110.00 |
| Thymidine | 0.70 |
| Amino Acids | |
| L-Alanine | 8.90 |
| L-Arginine | 200.00 |
| L-Arginine.HCl | 295.00 |
| L-Asparagine.H$_2$O | 15.01 |
| L-Asparagine (free base) | 50.00 |
| L-Aspartic Acid | 33.30 |
| L-Cystine.2HCl | 128.00 |
| L-Cysteine HCl.H$_2$O | 35.12 |
| L-Glutamic Acid | 34.70 |
| L-Glutamine | 1030.00 |
| Glycine | 47.50 |
| L-Histidine.HCl.H$_2$O | 63.00 |
| L-Histidine (free base) | 15.00 |
| L-Hydroxyproline | 20.00 |
| L-Isoleucine | 159.00 |
| L-Leucine | 168.10 |
| L-Lysine HCl | 222.50 |
| L-Methionine | 49.50 |
| L-Methionine | 49.50 |
| L-Phenylalanine | 86.00 |
| L-Proline | 54.50 |
| L-Serine | 82.50 |
| L-Threonine | 126.90 |
| L-Tryptophan | 23.00 |
| L-Tyrosinec.2Na.2H$_2$O | 140.81 |
| L-Valine | 125.70 |
| Vitamins | |
| Biotin | 0.2073 |
| D-Ca pantothenate | 4.75 |
| Choline Chloride | 21.00 |
| Folic Acid | 6.30 |
| i-Inositol | 60.20 |
| Niacinamide | 5.036 |
| Para-aminobenzoic Acid | 1.00 |
| Pyridoxine HCL | 1.06 |
| Pyridoxal HCl | 4.00 |
| Riboflavin | 0.637 |
| Thiamine HCl | 5.30 |
| Vitamin B$_{12}$ | 1.405 |

TABLE 3

Composition of cDRF

| Basal Components | 1× Liquid |
|---|---|
| DRF | 99% |
| ITS | 1% |
| Supplements | |
| Linoleic Acid | 5 µg/ml |
| Gentamycin | 100 µg/ml |
| Hydrocortisone | 40 ng/ml |
| Fibronectin | 5 µg/ml |
| Basic FGF | 10 ng/ml |
| Human Serum Albumin | 1 mg/ml | media ranging from liquid to semi-solid and includes solidified media and solid compositions suitable for reconstitution.

Supplementation of Basal Medium

Platelet-Derived Growth Factor (PDGF)

PDGF is a major mitogenic factor present in serum but not in plasma. PDGF is a dimeric molecule consisting of two structurally related chains designated A and B. The dimeric isoforms PDGF-M, AB and BB are differentially expressed in various cell types. In general, all PDGF isoforms are potent mitogens for connective tissue cells, including dermal fibroblasts, glial cells, arterial smooth muscle cells, and some epithelial and endothelial cell.

Recombinantly produced PDGF is commercially available from various sources. Human recombinant PDGF-BB (hrPDGF-BB) used in the examples below was purchased from R&D Systems (Minneapolis, Minn.; catalog # 220-BB) and reconstituted and handled according to the manufacturer's instructions. The E. coli expression of hrPDGF-BB and the DNA sequence encoding the 109 amino acid residue mature human PDGF-B chain protein (C-terminally processed from that ends with threonine residue 190 in the precursor sequence) is described by Johnson et al. (*EMBO J.*, 3: 921, 1984). The disulfide-linked homodimeric rhPDGF-BB consists of two 109 amino acid residue B chains and has molecular weight of about 25 kDa. The activity of PDGF is measured by its ability to stimulate $^3$H-thymidine incorporation in quiescent NR6R-3T3 fibroblast as described by Raines et al. (*Methods in Enzymology* 109: 749–773, 1985). The $ED_{50}$ for PDGF in this assay is typically 1.0–3 ng/ml.

In certain embodiments, DM of the invention is cDRF supplemented with PDGF and BMP or one or more lipids selected from the group consisting of stearic acid, myristic acid, oleic acid, linoleic acid, palmitic acid, palmitoleic acid, arachidonic acid, linolenic acid, cholesterol, and alpha-tocopherol acetate. The concentration of PDGF is chosen from 0.1–1 ng/ml, 1–5 ng/ml, 5–10 ng/ml, 10 ng/ml, 10–15 ng/ml, 15–50 ng/ml, and 50–100 ng/ml. In certain embodiments, cDRF is supplemented with 1 to 25 ng/ml, more preferably, 5 to 15 ng/ml and, most preferably, 10 ng/ml of PDGF. In a particular embodiment, the PDGF is PDGF-BB. Alternatively, PDGF could be of another type, e.g., PDGF-AB, PDGF-BB, or a mix of any PDGF types. In related embodiments, the DM of the invention further comprises additional supplements as described below.

Lipids

Lipids are important as structural components as well as potential energy sources in living cells. In vitro, most cells can synthesize lipids from glucose and amino acids present in the culture medium. However, if extracellular lipid is available, lipid biosynthesis is inhibited and the cells utilize free fatty acids, lipid esters, and cholesterol in the medium. Serum is rich in lipids and has been the major source of extracellular lipid for cultured cells. Chemically undefined lipid preparations based on marine oils have been found to be effective in promoting growth of cells in serum free-media in several systems (Weiss et al. (1990) *In Vitro* 26: 30A; Gorfien et al. (1990) *In Vitro* 26: 37A; Fike et al. (1990) *In Vitro* 26: 54A). Thus, supplementation of serum-free media with various lipids to replace those normally supplied by serum may be desirable.

Suitable lipids for use in the DM of this invention include stearic acid, myristic acid, oleic acid, linoleic acid, palmitic acid, palmitoleic acid, arachidonic acid, linolenic acid, cholesterol, and alpha-tocopherol acetate. In one embodiment, the basal medium is supplemented with the chemically defined lipid mixture (CDLM), shown in Table 4. CDLM is available from Gibco BRL (catalog # 11905–031). As supplied by Gibco BRL, in addition to the lipid components, CDLM contains ethanol (100 g/L) and emulsifiers Pluronic F68® (100 g/L) and Tween 80® (2.2 g/L).

In practicing the methods of the invention, the concentrations of individual lipid components of CDLM shown in Table 4 may be adjusted for specific cell culture conditions. Such adjustments can easily be made by a person skilled in the art using routine techniques. Furthermore, not all components of CDLM may be essential. A component or a subset of components is non-essential if, when its concentration is reduced, or the component is eliminated, the properties of the medium related to chondrocyte attachment, proliferation, and redifferentiation, remain substantially the same.

In certain embodiments, the DM of the invention comprises at least one, two, four, six, eight, or all lipid components of CDLM. In one embodiment, the DM comprises PDGF and CDLM as defined in Table 4. In other nonlimiting illustrative embodiments, the DM comprises PDGF and lipid combinations as set forth in Table 5.

TABLE 4

Composition of CDLM

| Lipid components | mg/L |
|---|---|
| DL-alpha-tocopherol acetate | 70 |
| Stearic acid | 10 |
| Myristic acid | 10 |
| Oleic acid | 10 |
| Linoleic acid | 10 |
| Palmitic acid | 10 |
| Palmitoleic acid | 10 |
| Arachidonic acid | 2 |
| Linolenic acid | 10 |
| Cholesterol | 220 |

In certain embodiments, the concentration (v/v) of lipids in the culture medium is chosen from 0.05–0.1%, 0.1–0.5%, 0.5%, 0.5–1%, 1–2%, and 2–5%. In certain other embodiments, DM is additionally supplemented with 1 to 25 ng/ml, more preferably, 5 to 15 ng/ml, and, most preferably, 10 ng/ml of PDGF. In a particular embodiment, DM comprises approximately 0.5% (v/v) CDLM, and 10 ng/ml PDGF.

The media can be used to seed, grow, and maintain chondrocytes capable of redifferentiation in culture without the use of serum. The stated ranges of concentrations of PDGF and lipids may need to be adjusted for specific cell culture conditions. Such adjustments can easily be made by a person skilled in art using routine techniques.

TABLE 5

Illustrative Lipid Combinations 1 cholesterol
2 cholesterol, arachidonic acid
3 cholesterol, arachidonic acid, linoleic acid
4 cholesterol, arachidonic acid, linoleic acid, linolenic acid
5 cholesterol, arachidonic acid, linoleic acid, linolenic acid, alpha-tocopherol acetate
6 cholesterol, arachidonic acid, linoleic acid, linolenic acid, alpha-tocopherol acetate, stearic acid
7 cholesterol, arachidonic acid, linoleic acid, linolenic acid, alpha-tocopherol acetate, stearic acid
8 cholesterol, arachidonic acid, linoleic acid, linolenic acid, alpha-tocopherol acetate, stearic acid, myristic acid
9 cholesterol, arachidonic acid, linoleic acid, linolenic acid, alpha-tocopherol acetate, stearic acid, myristic acid, oleic acid
10 cholesterol, arachidonic acid, linoleic acid, linolenic acid, alpha-tocopherol acetate, stearic acid, myristic acid, oleic acid, palmitic acid
11 cholesterol, arachidonic acid, linoleic acid, linolenic acid, alpha-tocopherol acetate, stearic acid, myristic acid, oleic acid, palmitic acid, palmitoleic acid
12 arachidonic acid, linoleic acid, linolenic acid, alpha-tocopherol acetate, stearic acid, myristic acid, oleic acid, palmitic acid, palmitoleic acid
13 arachidonic acid, linoleic acid, linolenic acid, stearic acid, myristic acid, oleic acid, palmitic acid, palmitoleic acid
14 arachidonic acid, linoleic acid, linolenic acid, stearic acid, myristic acid, oleic acid, palmitic acid
15 arachidonic acid, linoleic acid, linolenic acid, stearic acid, myristic acid, oleic acid
16 arachidonic acid, linoleic acid, linolenic acid, stearic acid, myristic acid
17 arachidonic acid, linoleic acid, linolenic acid, acetate, stearic acid
18 arachidonic acid, linoleic acid, linolenic acid, stearic acid
19 arachidonic acid, linoleic acid, linolenic acid
20 arachidonic acid, linoleic acid
21 arachidonic acid
22 cholesterol, linoleic acid
23 cholesterol, linoleic acid, linolenic acid
24 cholesterol, linoleic acid, linolenic acid, stearic acid
25 cholesterol, linoleic acid, linolenic acid, stearic acid, myristic acid
26 cholesterol, linoleic acid, linolenic acid, stearic acid, myristic acid, oleic acid
27 cholesterol, linoleic acid, linolenic acid, stearic acid, myristic acid, oleic acid, palmitic acid
28 cholesterol, linoleic acid, linolenic acid, stearic acid, myristic acid, oleic acid, palmitic acid, palmitoleic acid
29 cholesterol, linoleic acid, linolenic acid, alpha-tocopherol acetate, stearic acid, myristic acid, oleic acid, palmitic acid, palmitoleic acid
30 linoleic acid
31 cholesterol, linoleic acid
32 cholesterol, arachidonic acid, linoleic acid
33 cholesterol, arachidonic acid, linoleic acid, linolenic acid
34 cholesterol, arachidonic acid, linoleic acid, linolenic acid, alpha-tocopherol acetate
35 cholesterol, arachidonic acid, linoleic acid, linolenic acid, alpha-tocopherol acetate, stearic acid
36 cholesterol, arachidonic acid, linoleic acid, linolenic acid, alpha-tocopherol acetate, stearic acid, myristic acid
37 cholesterol, arachidonic acid, linoleic acid, linolenic acid, alpha-tocopherol acetate, stearic acid, myristic acid, oleic acid
38 cholesterol, arachidonic acid, linoleic acid, linolenic acid, alpha-tocopherol acetate, stearic acid, myristic acid, oleic acid
39 cholesterol, arachidonic acid, linoleic acid, linolenic acid, alpha-tocopherol acetate, stearic acid, myristic acid, oleic acid, palmitic acid, palmitoleic acid
40 linolenic acid
41 cholesterol, linolenic acid
42 cholesterol, alpha-tocopherol acetate, stearic acid, myristic acid, oleic acid, palmitic acid, palmitoleic acid
43 cholesterol, alpha-tocopherol acetate
44 cholesterol, stearic acid, myristic acid, oleic acid, palmitic acid, palmitoleic acid
45 stearic acid, myristic acid, oleic acid, palmitic acid, palmitoleic acid
46 cholesterol, myristic acid, oleic acid, palmitic acid, palmitoleic acid TABLE 5-continued Illustrative Lipid Combinations 47 cholesterol, oleic acid, palmitic acid, palmitoleic acid
48 cholesterol, stearic acid, myristic acid, oleic acid, palmitic acid, palmitoleic acid
49 cholesterol, myristic acid, oleic acid, palmitic acid
50 cholesterol, arachidonic acid, linoleic acid, linolenic acid, palmitic acid, palmitoleic acid Chondrocytes and Other Suitable Cells The present invention is generally suitable for ex vivo proliferation of cells capable of producing cartilaginous tissue. Chondrocytes are cells found in various types of cartilage, e.g., hyaline cartilage, elastic cartilage, and fibrocartilage. Chondrocytes are mesenchymal cells that have a characteristic phenotype based primarily on the type of extracellular matrix they produce. Precursor cells produce type I collagen, but when they become committed to the chondrocyte lineage, they stop producing type I collagen and start synthesizing type II collagen, which constitutes a substantial portion of the extracellular matrix. In addition, committed chondrocytes produce proteoglycan aggregate, called aggrecan, which has glycosaminoglycans that are highly sulfated.

Chondrocytes can be isolated from any mammal, including, without limitation, human, orangutan, monkey, chimpanzee, dog, cat, rat, rabbit, mouse, horse, cow, pig, elephant, etc.

Chondrocytes used in the present invention can be isolated by any suitable method. Various starting materials and methods for chondrocyte isolation are well known in the art (Freshney (1987) Culture of Animal Cells: A Manual of Basic Techniques, 2d ed. A. R. Liss, Inc., New York, pp. 137–168; Klagsburn (1979) *Methods Enzymol.* 58: 560–564). By way of example, articular cartilage can be harvested from femoral condyles of human donors, and chondrocytes can be released from the cartilage by overnight digestion in 0.1% collagenase/DMEM. The released cells are expanded as primary cells in a suitable medium such as the DM of this invention or DMEM containing 10% FBS. Cells can be passaged at 80–90% confluence using 0.05% trypsin-EDTA, diluted for subculture, and reseeded for second and subsequent passages to allow for further expansion. At any time, trypsinized cells can be frozen in DMEM containing .10% DMSO and 40% HSA or in other compositions known in the art, e.g., as described in U.S. Pat. No. 6,365,405.

It may be desirable in certain circumstances to utilize chondrocyte progenitor stem cells such as mesenchymal stem cells rather than cells from cartilage biopsies that are already differentiated into chondrocytes. Examples of tissues from which such stem cells can be isolated include placenta, umbilical cord, bone marrow, skin, muscle, periosteum, or perichondrium. Chondrocytes can be obtained by inducing differentiation of such cells into chondrocytes in vitro.

The term "chondrocytes," as used herein, refers not only to mesenchymal stem cells, but also to cells that can be trans-differentiated into chondrocytes, for example, adipocytes, osteocytes, fibroblasts, and myocytes. The term "chondrocytes" also refers to chondrocytes that are passaged or dedifferentiated.

The term "low density" refers to seeding densities less than 20,000 cells/cm$^2$.

The methods of this invention are suitable for cells growing in cultures under various conditions including, but not limited to, monolayers, multilayers, on solid support, in suspension, and in 3D cultures.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

Various aspects of the invention are further described and illustrated in the examples presented below.

Example 1

Human articular cartilage biopsy samples from donors of 16–51 years of age were trimmed of extraneous material, minced and subjected to enzymatic digestion using 0.25% protease from Bascilus Thermopropolipycus for 1–2 hrs followed by an overnight digestion in 0.1% collagenase/DMEM at 37° C. Isolated articular chondrocytes were washed twice in DMEM containing 10% human serum albumin (DMEM/10% HSA). The isolated primary human articular chondrocytes (HAC) were seeded at 5,000–6,000 cells/cm$^2$ in T75 flasks using the following separate media conditions:

1) DMEM/10% FBS (DMEM supplemented with 10% fetal bovine serum and 100 μg/ml gentamycin);
2) cDRF (as defined in Table 3);
3) cDRF/P (cDRF supplemented with 10 ng/ml PDGF);
4) cDRF/L (cDRF supplemented with 5 μl/ml CDLM (as defined in Table 4)); and
5) cDRF/P/L (cDRF supplemented with 10 ng/ml PDGF and 5 μl/ml CDLM)

Two flasks were used per each condition. At the end of each passage, nearly confluent cells were harvested by trypsinization, counted, washed in DMEM/10% HSA and reseeded at 5,000–6,000 cells/cm$^2$ in the corresponding media. Cell yield was calculated as the average of duplicate samples for each condition. A comparison of cell yields at the end of each passage for chondrocytes propagated under media condition defined above is represented in Table 6. The results of this experiment demonstrate that regardless of the passage number, cell yields were higher for chondrocytes passaged in cDRF/P/L, as compared to either DMEM/10% FBS or cDRF. The effect was more pronounced for higher passage numbers.

TABLE 6

| | Cell Yield per T75, x10$^7$ | | | | |
|---|---|---|---|---|---|
| Passage | 1 | 2 | 3 | 4 | 5 |
| Medium | | | | | |
| DMEM/10% FBS | 0.95 | 0.6 | 0.25 | 0.24 | 0.3 |
| cDRF | 0.59 | 0.75 | 0.90 | 1.05 | 0.8 |
| cDRF/P/L | 1.9 | 2.8 | 1.2 | 2.25 | 2.05 |

Example 2

Hyaline cartilage biopsy samples collected from multiple donors were used to compare cell yields as a function of the passage number for chondrocytes cultured in DMEM/10% FBS or in a completely defined serum-free medium according to this invention. Samples were collected and treated as described in Example 1. Isolated chondrocytes were washed twice in DMEM containing 10% human serum albumin (DMEM/10% HSA). The isolated primary human articular chodrocytes (HAC) were seeded at 6,000 cells/cm$^2$ in T75 flasks using the following media conditions:

1) DMEM/10% FBS (DMEM supplemented with 10% fetal bovine serum and 100 μg/ml gentamycin); and
2) cDRF/P/L (cDRF supplemented with 10 ng/ml PDGF and 5 μl/ml CDLM)

At the end of each passage nearly confluent cells were harvested by trypsinization, counted, washed in DMEM/10% HSA and reseeded at 6,000 cells/cm$^2$ in respective media. A comparison of cell yields at the end of each passage for chondrocytes propagated in DMEM/10% FBS or cDRF/P/L is shown in Table 7. Cell yields were higher in cDRF/P/L as compared to DMEM/10% FBS for cells in passages 1–3, and significantly higher (p=0.05) for cells in passage 4.

TABLE 7

| Passage | 1 | 2 | 3 | 4 |
|---|---|---|---|---|
| | DMEM/10% FBS | | | |
| Cell Yield (x10$^4$/cm$^2$) | 7.5 ± 2.3 | 8.5 ± 2.4 | 5 ± 2.7 | 4 ± 2.0 |
| Number of Samples | 9 | 8 | 5 | 3 |
| | cDRF/P/L | | | |
| Cell Yield (x10$^4$/cm$^2$) | 9.6 ± 7.0 | 12.5 ± 4.5 | 9.0 ± 5.0 | 14.0 ± 6.3 |
| Number of Samples | 8 | 8 | 3 | 3 |
| T-test p-value | 0.43 | 0.07 | 0.10 | 0.05* |

Example 3

Figure 1:
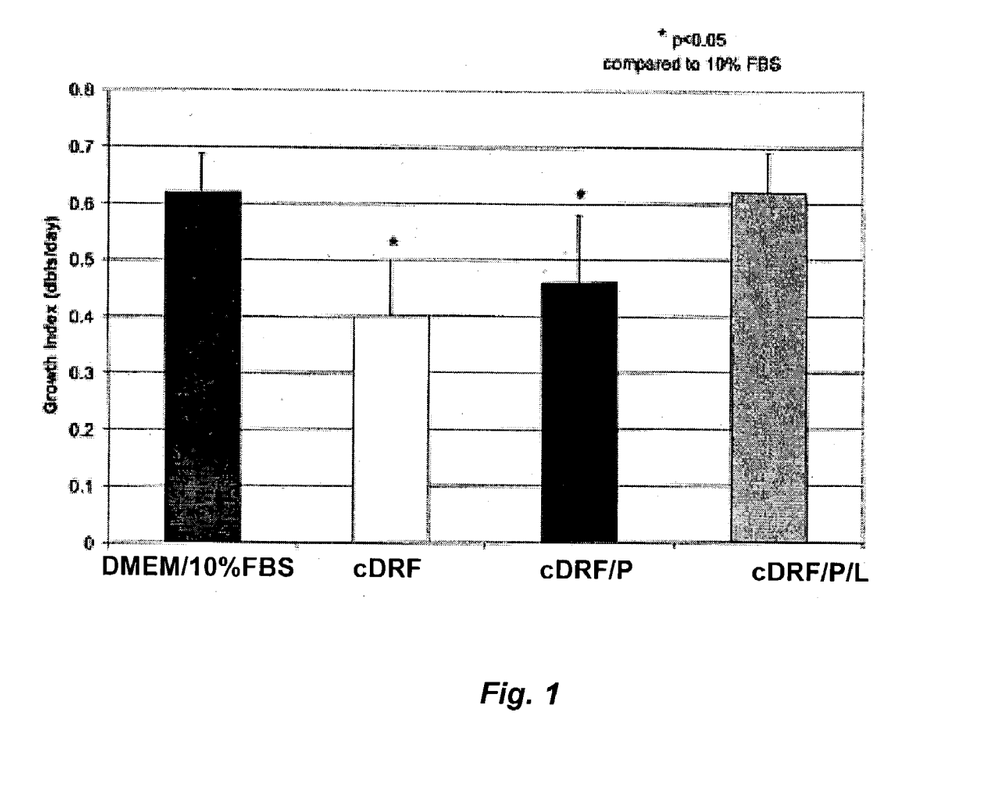
FIG. 1 is a diagram of growth index for human articular chondrocytes propagated ex vivo for four passages in DMEM/10% FBS or cDRF (defined in Table 3), cDRF supplemented with 10 ng/ml PDGF, and cDRF supplemented with 10 ng/ml PDGF and 5 µl/ml of the chemically defined lipid mixture (CDLM) set forth in Table 4.

In this experiment, human articular chondrocytes from three donors, ages 16, 22, and 55, were isolated and treated as described in Example 1. Chondrocytes were seeded at 6,000 cells/cm$^2$ in T75 flasks and grown in DMEM/10% FBS until near confluence. The cells were then harvested by trypsinization, washed in seeding media, and immediately frozen in 10% DMSO/40% HSA/50% DMEM. For the second passage, ampules of frozen cells were thawed out, rinsed in DMEM/10% HSA and reseeded at 3,000–4,000 cells/cm$^2$ in the following media: 1) DMEM/10% FBS; 2) cDRF; 3) cDRF/P; and 4) cDRF/P/L (see Example 1 for the description of the media). Two flasks were used per each set of media conditions. At the end of each passage nearly confluent cells were harvested by trypsinization, washed in DMEM/10% HSA and reseeded in the corresponding media. At the end of the third passage, cells were harvested and counted. Growth index expressed as a number of doublings per day at the end of a seven-day period was calculated as the mean value for the three donor samples, with each sample being represented by the average of duplicates derived from the donor. A comparison of growth index for chondrocytes propagated in DMEM/10% FBS and in completely defined serum-free media is illustrated in FIG. 1. Growth index for chondrocytes propagated in DMEM/10% FBS and those propagated in cDRF/P/L were comparable whereas cells propagated in cDRF/P or cDRF had slightly lower growth index. Chondrocytes grown as monolayer in DM of the invention did not have the typical fibroblastic morphology when compared with chondrocytes grown in DMEM/10% FBS, but had a very distinct cell shape with well defined borders.

Example 4

Figure 2:
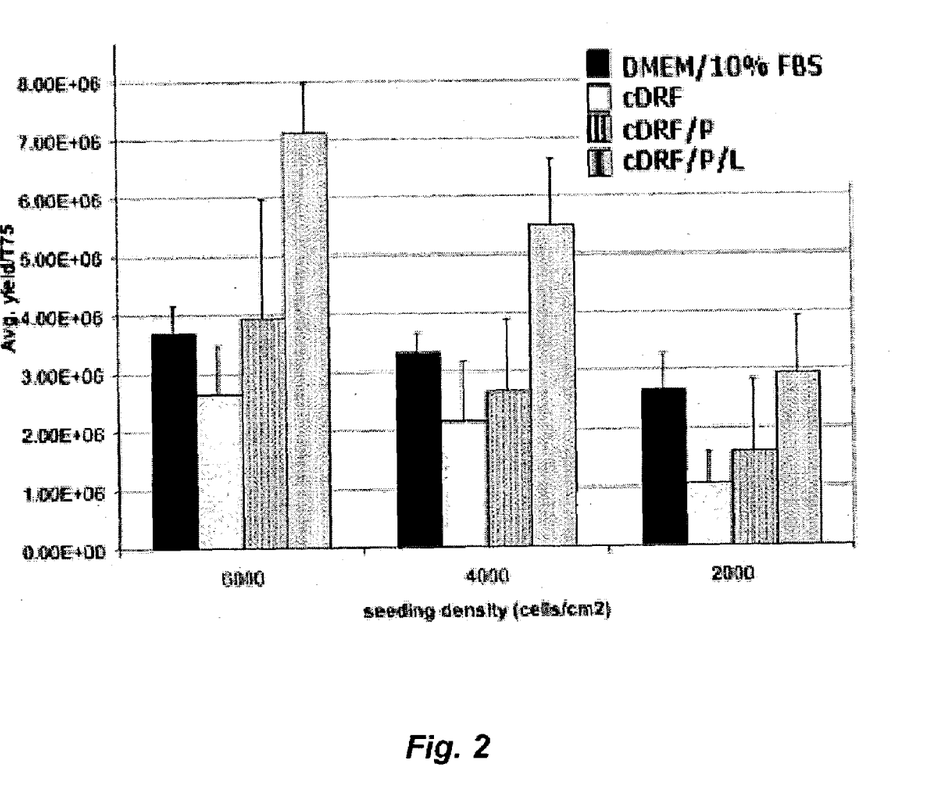
FIG. 2 illustrates cell yields for human articular chondrocytes plated at various seeding densities and propagated ex vivo for four passages in DMEM/10% FBS or in the defined serum-free media as follows: cDRF; cDRF supplemented with 10 ng/ml PDGF; and cDRF supplemented with 10 ng/ml PDGF and 5 µl/ml CDLM.

In this experiment, the dependence on the seeding density was investigated. Human hyaline articular chondrocytes were obtained from the same donors and treated as described Example 3, except each sample was split into three to be seeded at 6,000; 4,000, and 2,000 cells/cm$^2$. At the end of each passage, cells were reseeded at the original seeding density of that set. At the end of the third passage, cells were harvested, counted and cell yield was calculated for chondrocytes propagated in DMEM/10% FBS or in DM of this invention. The results of the experiment are presented in FIG. 2. Chondrocytes grown in cDRF/P/L had at least comparable or higher yields than cells grown in DMEM/10% FBS or cDRF/P, whereas cells propagated in cDRF had slightly lower yields as compared to DMEM/10% FBS. The difference was more pronounced for cells passaged at seeding density of 6,000 cells/cm$^2$. Additionally, cells grown in cDRF or cDRF/P had higher yields at higher seeding densities.

Example 5

To assess the redifferentiation potential of chondrocytes after their expansion in monolayer culture in DM of this invention, the chondrocytes' capacity to form cartilaginous tissue was examined. Chondrocytes were isolated and treated as described in Example 2. At the end of the second passage chondrocytes were trypsinized, rinsed in DMEM/10% FBS and seeded as described below on Millicell-CM® filter inserts (12 mm diameter, 0.4 µm pore size, Millipore Corp., Bedford, Mass.). The filters were pre-coated with type II collagen (0.5 mg/ml 0.012N HCl) [Sigma St. Louis, Mo.]. Chondrocytes were seeded at 2×10$^6$ cells/cm$^2$ on top of the filter in DMEM/20% FBS or in a DMEM-based differentiation medium (DMEM supplemented with 2 mg/ml HSA, 5 µg/ml linoleic acid, 2% ITS). The cultures were maintained at 37° C. in a humidified atmosphere supplemented with 5% CO$_2$. After three days in culture 100 µg/ml ascorbic acid, 5 ng/ml TGF-β2 and 10 ng/ml PDGF-BB were added to the media. The media were changed every two days. After 1 week, the chondrocyte cultures on the filter inserts were harvested at selected intervals and fixed in 10% formalin, embedded in paraffin and cut in 5 µm sections that were then stained with toluidine blue or safranin-O. These reagents stain sulphated proteoglycans. Sulphated glycosaminoglycans were quantified using a modified dimethylmethylene blue assay according to the procedure described by Farndale et al. (*Biochimica et Biophyca Acta* 883:173–177, 1986).

Immunohistochemical analysis on the paraffin-embedded sections was performed to analyze expression of type II collagen. Primary antibodies for type II collagen (Biodesign International, Kennebunkport, Me.) were used at 1:50 dilution. The reaction was carried out in a humid atmosphere at 37° C. for one hour. The tissue sections were then washed 3 times in Phosphate Buffered Saline (PBS) and incubated with a 1:200 dilution of rhodamine-conjugated goat anti-rabbit IgG in PBS as a secondary antibody, under the same conditions as described for the primary antibodies. Hoechst dye at 1 µg/ml was included in some experiments with the secondary antibody for nuclear staining. The sections were washed three times in PBS and examined under a fluorescence microscope.

Histological examination of the cultures showed that the chondrocytes passaged in cDRF/P/L accumulated an extracellular matrix, which contained proteoglycans and collagen, and formed a continuous layer of cartilaginous tissue. These chondrocytes showed an increase in the amount of tissue produced and the matrical staining of proteoglycans when compared with chondrocyted propagated with DMEM/10% FBS. The cells propagated in cDRF/P/L readily underwent differentiation from a monolayer to round cells with lacunae chondrogenic morphology and expressed more type II collagen as compared to DMEM/10% FBS. The results of this experiment demonstrate that chondrocytes propagated in DM of the invention, are capable of re-expressing their chondrocyte phenotype, i.e., they retain their redifferentiation potential. The results also demonstrate the feasibility of producing preformed cartilage grafts from propagated chondrocytes isolated and expanded in DM of the invention.

Example 6

Normal adult human articular chondrocytes dedifferentiate as a consequence of expansion in monolayer in vitro. To confirm that chondrocytes cultured in DM of the invention have retained their capacity to redifferentiate, a TaqMan analysis of gene expression of cartilage-specific markers was performed. The analysis of gene expression begins with the isolation of quality total RNA from ex vivo formed cartilagenous tissue and normal articular cartilage.

Initially, chondrocytes were isolated and treated and expanded in DMEM/10% FBS or cDRF/P/L described in Example 2. These cultures were then harvested at 1, 2, 3, and 4 weeks from seeding on the filter inserts. Subsequently, chondrocytes cultures were grown on Millicell-CM® filter inserts as described in Example 5. Gene expression was analyzed for the following proteins: aggrecan, type I collagen, type II collagen, type X collagen, osteocalcin, osteopontin, and versican.

Total RNA was isolated using a modification of a published protocol (Reno et al. (1997) *Biotechniques* 22: 1082–1086). First total RNA is isolated from the tissue using the TRIzol reagent (catalog # 15596–026, Invitrogen Life Technologies, Carlsbad, Calif.) along with mechanical homogenization using a handheld tissue homogenizer. The isolated RNA was resuspended in 10 µl of nuclease-free water and purified over a RNeasy Mini spin column (catalog # 74104, QIAGEN, Valencia, Calif.) following a protocol as supplied by the manufacturer. Contaminating genomic DNA is removed using DNA-free kit (catalog # 1906, Ambion, Austin, Tex.). An equal amount of total RNA was taken from each sample and reverse-transcribed (RT) using beads with an oligo-dT primer (catalog # 27-9264-01, Amersham Biosciences, Piscataway, N.J.). A Picogreen assay ( catalog # P-7589, Molecular Probes, Eugene, Oreg.) was performed to measure the efficiency of the RT reaction. Next, a TaqMan assay was performed to quantify of the absolute copy number of each gene using 25 ng of starting material from each sample. The number of gene copies was determined for each gene using a standard curve created with commercially available plasmid standards. The final results were adjusted in accordance with results of the PicoGreen assay.

Figure 3A:
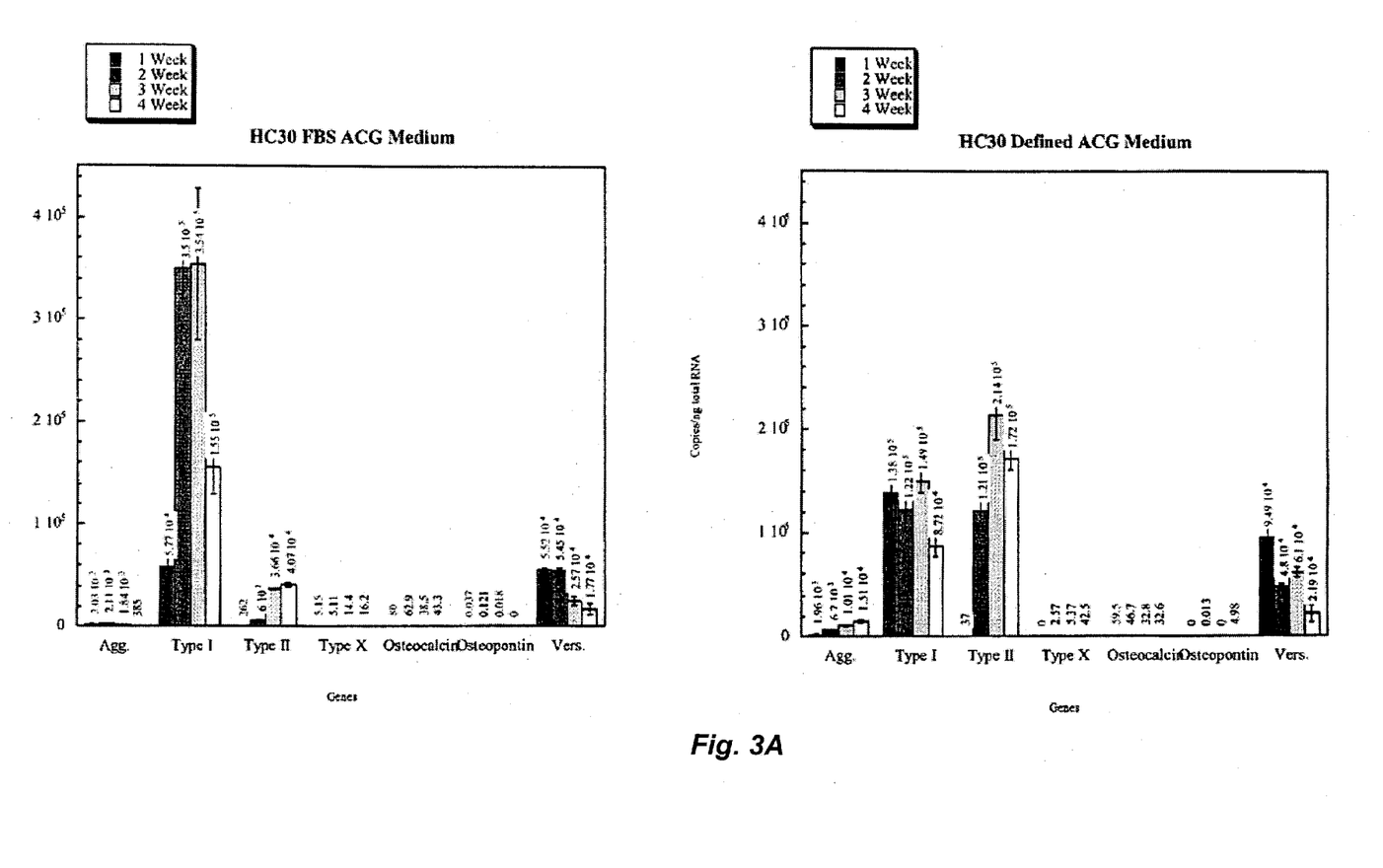
FIGS. 3A and 3B depict results of a TaqMan analysis of genes expressed by chondrocytes expanded in DMEM/10% FBS or in cDRF supplemented with 10 ng/ml PDGF and 5 µl/ml CDLM.
Figure 3B:
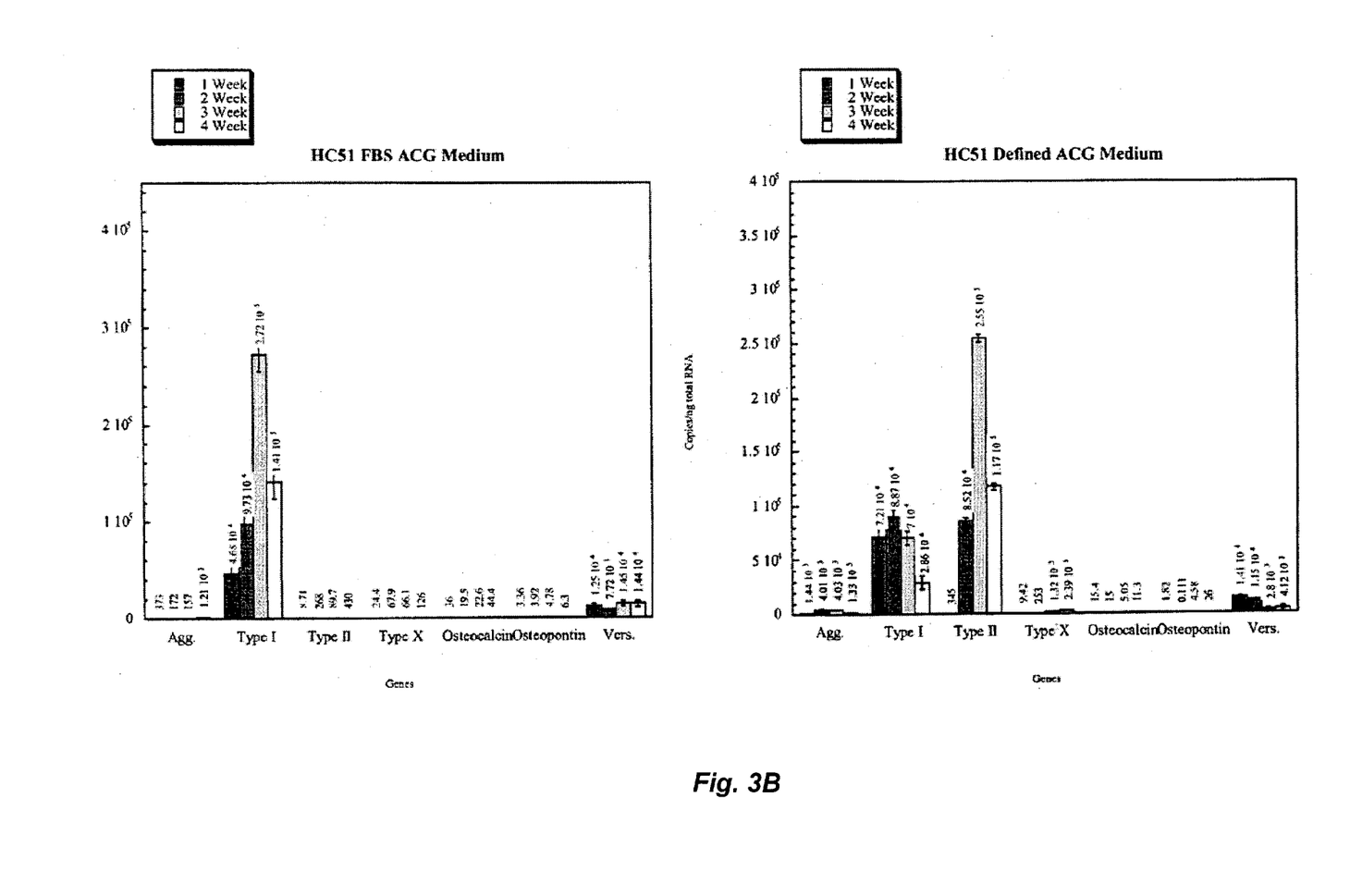

The results of a TaqMan assays for samples from two subjects are presented in FIGS. 3A and 3B. These results demonstrate a sustained (2–4 weeks) elevated expression of the type II collagen gene, a major marker for articular cartilage, in cells propagated in DMEM/P/L. The results of this experiment confirm that that chondrocytes propagated in DM of the present invention retain their capacity to re-express the chondrocyte phenotype. The results also demonstrate the feasibility of producing preformed cartilage grafts from propagated chondrocytes isolated and expanded in DM of the invention.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention.

Unless otherwise indicated, all numbers expressing quantities of ingredients, cell culture conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. A skilled artisan will recognize that many other embodiments are encompassed by the claimed invention and that it is intended that the specification and examples be considered as exemplary only, with a true scope and spirit of the invention being indicated by the following claims.

The invention claimed is:

1. A method for ex vivo propagation of chondrocytes, comprising the step of incubating the chondrocytes with a culture medium comprising a basal medium, PDGF, and at least four lipids selected from the group consisting of stearic acid, myristic acid, oleic acid, linoleic acid, palmitic acid, palmitoleic acid, arachidonic acid, linolenic acid, cholesterol, and alpha-tocopherol acetate.

2. A method for ex vivo propagation of chondrocytes, comprising the step of incubating the chondrocytes with a culture medium comprising a basal medium, PDGF, and at least six lipids selected from the group consisting of stearic acid, myristic acid, oleic acid, linoleic acid, palmitic acid, palmitoleic acid, arachidonic acid, linolenic acid, cholesterol, and alpha-tocopherol acetate.

3. A method for ex vivo propagation of chondrocytes, comprising the step of incubating the chondrocytes with a culture medium comprising cDRF, PDGF, stearic acid, myristic acid, oleic acid, linoleic acid, palmitic acid, palmitoleic acid, arachidonic acid, linolenic acid, cholesterol, and alpha-tocopherol acetate.

4. A serum-free medium comprising a basal medium, PDGF, stearic acid, myristic acid, oleic acid, linoleic acid, palmitic acid, palmitoleic acid, arachidonic acid, linolenic acid, cholesterol, and alpha-tocopherol acetate.

5. The medium of claim 4, wherein the concentration of PDGF is chosen from 0.1–1 ng/ml, 1–5 ng/ml, 5–10 ng/ml, 10 ng/ml, 10–15 ng/ml, 15–50 ng/ml, and 50–100 ng/ml.

6. The method of claim 5, wherein the PDGF is chosen from PDGF-BB, PDGF-AB, and PDGF-AA.

7. The medium of claim 4, which further comprises the chemically defined lipid mixture (CDLM) as defined in Table 4.

8. The medium of claim 4, wherein the concentration of CDLM in the culture medium is chosen from 0.05–0.1%, 0.1–0.5%, 0.5%, 0.5–1%, 1–2%, and 2–5%.

9. The medium of claim 4, which further comprises ITS, hydrocortisone, fibronectin, bFGF, and albumin.

10. The medium of claim 4, wherein the basal medium comprises DRF as defined in Table 2.

11. The medium of claim 4, wherein the basal medium comprises cDRF as defined in Table 3.

12. The medium of claim 4, which further comprises one or more supplements selected from the group consisting of BMP, TGF-$\beta$, IGF, and insulin.

13. The medium of claim 4, wherein the BMP is BMP-4 or BMP-6.

14. The medium of claim 4, which comprises cDRF as defined in Table 3, 0.5% CDLM as defined in Table 4, and 10 ng/ml PDGF.

15. The medium of claim 14, wherein the PDGF is PDGF-BB.

16. A composition comprising a chondrocyte and a culture medium comprising a basal medium, PDGF, and the chemically defined lipid mixture (CDLM) as defined in Table 4, wherein the concentration of CDLM is 0.5%.

17. A composition comprising a human chondrocyte and a culture medium comprising a basal medium, cDRF as defined in Table 3, 0.5% CDLM as defined in Table 4, and 10 ng/ml PDGF.

* * * * *